(12) United States Patent
Echeverri L. et al.

(10) Patent No.: US 8,895,627 B2
(45) Date of Patent: Nov. 25, 2014

(54) METHOD TO ELICIT TOMATO RESISTANCE TO FUNGAL DISEASE

(75) Inventors: Luis F. Echeverri L., Medellín (CO); James A. Jimenez M., Medellin (CO); Luis F. Torres, Medellín (CO)

(73) Assignee: Ecoflora Agro SAS, Rionegro, Antioquia (CO)

( * ) Notice: Subject to any disclaimer, the term of this patent is extended or adjusted under 35 U.S.C. 154(b) by 0 days.

(21) Appl. No.: 13/041,400

(22) Filed: Mar. 6, 2011

(65) Prior Publication Data

US 2012/0225780 A1    Sep. 6, 2012

(51) Int. Cl.
*A61K 31/075* (2006.01)
*A01N 65/28* (2009.01)
*A01N 43/90* (2006.01)
*A01N 65/00* (2009.01)

(52) U.S. Cl.
CPC ............... *A01N 65/00* (2013.01); *A01N 65/28* (2013.01); *A01N 43/90* (2013.01)
USPC ........................................................ 514/715

(58) Field of Classification Search
None
See application file for complete search history.

(56) References Cited

U.S. PATENT DOCUMENTS 6,765,085 B2 * 7/2004 Chory et al. .................. 530/350
7,863,350 B2 * 1/2011 Brander et al. ............... 523/122
7,892,581 B2   2/2011 Kvitnitsky et al.

OTHER PUBLICATIONS

Tzortzakis, Maintaining postharvest quality of fresh produce with volatile compounds, Innovative Food Science & Emerging Technologies vol. 8 Issue 1, Mar. 2007, p. 111-116.*
Abd-Alla, M.A., et al., "Formulation of Essential Oils and Yeast for Controlling Postharvest Decay of Tomato Fruits," *Plant Pathology Bulletin* 18:23-33, Taizhong Shi, China (2009).
Hall, D.J., "Postharvest Treatment of Florida Fresh Market Tomatoes with Fungicidal Wax to Reduce Decay," *Proc. Fla. State Hort. Soc.* 102:365-367, Florida State Horticultural Society, United States (1989).
Hyldgaard, M., et al., "Essential oils in food preservation: mode of action, synergies, and interactions with food matrix components," *Frontiers in Microbiology* 3:1-24, Frontiers Research Foundation, Switzerland (2012).
Martínez, J.A., "Natural Fungicides Obtained from Plants," *Fungicides for Plant and Animal Diseases*, Dhanasekaran, D., (Ed.) InTech, Rijeka, Croatia (2012).

* cited by examiner

*Primary Examiner* — Alton Pryor
(74) *Attorney, Agent, or Firm* — Sterne, Kessler, Goldstein & Fox P.L.L.C.

(57) ABSTRACT

The present invention provides an essential oil containing cineole for eliciting tomato resistance to disease by fungal infection. The present invention also provides a method to elicit tomato resistance to disease by fungal infection.

8 Claims, No Drawings

METHOD TO ELICIT TOMATO RESISTANCE TO FUNGAL DISEASE

BACKGROUND OF THE INVENTION

1. Field of the Invention

The present invention is related to the use of essential oil vapors to elicit fruit resistance to disease by fungal infection.

2. Description of Prior Art

Tomato fruit decay after harvest is a prevalent problem that causes significant economic losses. Tomato fruit decay is mainly caused by fungus, e.g., *Botrytis cinerea, Rhizopus stolonifer,* and *Alternaria alternate, Colletotrichum coccodes,* etc. Usually, tomato fruit decay may be prevented by applying directly to the fruits antifungal agents (pesticides or natural agents).

The application of antifungal agents to fruits has several disadvantages. In the case of pesticides, their use is limited because of toxicity which may require complicated formulations such as applying a pesticide in a wax layer. See Hall, D. J., Post Harvest Treatment of Florida Fresh Market Tomatoes with Fungicidal Wax to Reduce Decay, Proc. Fla. State, Hort. Soc. 102:365-367, 1989.

Natural agents are an alternative. However, the antifungal effect of natural agents may require application of high doses, as is the case for essential oils. For example, to avoid application of high doses of essential oils to prevent tomato decay, antagonists to decay causing pathogens have been combined with a low dose of an essential oil. See El-Gamal et al., Formulation of Essential Oils and Yeast for Controlling Post-Harvest Decay of Tomato Fruits, Plant Pathology Bulletin, 18:23-33, 2009.

In any case of antifungal agents, the antifungal has to be applied to the tomato directly. The present invention overcomes the need to apply an antifungal agent to a fruit. Instead, by means of the present invention, fruit resistance to decay causing pathogens is elicited.

SUMMARY OF THE INVENTION

The present invention provides an essential oil containing cineole for eliciting tomato resistance to disease by fungal infection. The present invention also provides a method to elicit tomato resistance to disease by fungal infection.

Specifically, the method to elicit tomato resistance to disease by fungal infection comprises exposing at least one tomato to an essential oil vapor, wherein the essential oil contains cineole.

In one aspect of the method of the present invention, the essential oil is eucalyptus oil.

In another aspect of the method of the present invention, the essential oil vapor concentration is 500 ppm.

In the most preferred aspect of the present invention, the essential oil containing cineole for eliciting tomato resistance to disease by fungal infection turns into a vapor form in the environment surrounding the tomato.

In one aspect of the essential oil of the present invention, said essential oil is eucalyptus oil.

In one additional aspect of the essential oil of the present invention, the concentration of the vapor derived from said essential oil is 500 ppm.

Additional objectives and advantages of the present invention will be more evident in the detailed description of the invention and the claims.

DETAILED DESCRIPTION OF THE INVENTION

The present invention provides a method to elicit tomato resistance to disease by fungal infection, wherein the method comprises exposing at least one tomato to an essential oil vapor, wherein the essential oil contains cineole.

For purposes of the present invention, the term "to elicit . . . resistance to disease by fungal infection" means that a tomato or a fruit, exposed to a cineole containing essential oil, becomes less susceptible to decay when said tomato or fruit is exposed to a fungus, wherein the essential oil or the essential oil vapor does not have any effect over said fungus.

The term essential oil vapor defines the gaseous state of the essential oil, wherein said essential oil gaseous state occurs because of transformation from the essential oil liquid state due to the volatile nature of essential oil.

In one aspect of the method of the present invention, the essential oil is eucalyptus oil.

In another aspect of the method of the present invention, the essential oil vapor concentration is 500 ppm.

In the most preferred aspect of the present invention, the essential oil containing cineole for eliciting tomato resistance to disease by fungal infection turns into a vapor form in the environment surrounding the tomato.

In one aspect of the essential oil of the present invention, said essential oil is eucalyptus oil.

However, for purposes of the invention, the term essential oil encompasses any essential oil containing cineole that is used to induce or elicit tomato resistance to disease or decay caused by fungal infection.

In one additional aspect of the essential oil of the present invention, the concentration of the vapor derived from said essential oil is 500 ppm.

A concentration of 500 ppm means that the essential oil vapor has a concentration of 500 parts per million in the immediate surroundings of a fruit or a tomato.

Although the description presents preferred embodiments of the present invention, additional changes may be made in the form and disposition of the parts without deviating from the ideas and basic principles encompassed by the claims.

EXAMPLES

Healthy tomato fruits were collected from plants free of treatment with pesticides or any other control agent. According to the Jaramillo scale (Jaramillo et al., 2007) the tomatoes were at level 3 of maturation. The tomatoes were superficially disinfected and were put in plastic closed boxes (each box: 10 cm×17 cm 33 cm). There were eight (8) tomatoes per plastic box.

Three sets (two boxes per set) of boxes with tomatoes were prepared as follows:

Set No. 1:
  A) Each tomato was punctured multiple times with a sterile needle. A small agar disk with *Botrytis cinerea* ($1\times10^6$ conidia per disk) was put over each puncture.
  B) 2.805 ml of liquid pure eucalyptus oil in a Petri dish (for a final concentration of 500 ppm once the eucalyptus oil has completely evaporated, since there were no remains at all of liquid eucalyptus oil) was put inside de box 48 hours before infection with *Botrytis,* 24 hours before the infection, at time 0 (time of the infection), and 24 hours after the infection.

Set No. 2:
  A) Tomatoes were not infected.
  B) 2.805 ml of sterile water in a Petri dish was put inside de box 48 hours before infection with *Botrytis,* 24 hours before the infection, at time 0 (time of the infection), and 24 hours after the infection.

Set No. 3:
   A) Each tomato was punctured multiple times with a sterile needle. A small agar disk with *Botrytis cinerea* ($1\times10^6$ conidia per disk) was put over each puncture.
   B) 2.805 ml of sterile water in a Petri dish was put inside de box 48 hours before infection with *Botrytis*, 24 hours before the infection, at time 0 (time of the infection), and 24 hours after the infection.

After 13 days of the infection all tomatoes were examined. The results are shown in table 1.

TABLE 1

| Set No. | Number of diseased tomatoes | Percentage disease free (Healthy tomatoes) |
|---|---|---|
| 1 | 1 out of 16 | 93.75% |
| 2 | 0 | 100% |
| 3 | 16 out of 16 | 0% |

To discard a direct fungicide effect on *botrytis cinerea* by eucalyptus oil, the following experiment was made:
1. *Botrytis cinerea* spore were grown in appropriate culture medium enriched with eucalyptus. Result: There is not growth inhibition of *Botrytis cinerea* fungus.
2. An open Petri dish with appropriate culture medium inoculated with *Botrytis cinerea* spores was put in the empty plastic boxes (each box: 10 cm×17 cm 33 cm). 2.805 ml of liquid pure eucalyptus oil in a Petri dish (for a final concentration of 500 ppm once the eucalyptus oil has completely evaporated) was put inside de box 48 hours before infection with *Botrytis*, 24 hours before the infection, at time 0 (time of the infection), and 24 hours after the infection. Result: There is not growth inhibition of *Botrytis cinerea* fungus.

When tomatoes of Set No. 1 were examined after the above described experiments, it was observed that the punctures healed, that the fungus did not colonized the tomato tissues with no disease or decay. The tomatoes internal and external tissues were healthy and without any alterations regarding color, brightness, odor or texture.

When the eucalyptus oil used in the experiments was analyzed by gas chromatography, the main component (80+%) was 1-8 cineole.

The results of the experiments described above show that there is not direct fungicide effect of an essential oil, eucalyptus oil, on *botrytis cinerea*. In spite of not fungicide effect, the tomatoes, when exposed to a 500 ppm saturated environment with eucalyptus oil, became resistant to disease or decay when contaminated with *botrytis cinerea* conidia. Somehow, the tomatoes developed less susceptibility to diseased if contaminated by the fungus.

The invention claimed is:

1. A method to elicit tomato resistance to *Botrytis cinerea* fungal infection, wherein the method consists essentially of exposing at least one tomato to an essential oil, wherein the essential oil consists essentially of 80% cineole, wherein the essential oil is applied in a sufficient amount to elicit tomato resistance to *Botrytis cinerea* infection, and wherein the essential oil has no direct antifungal effect against *Botrytis cinerea*.

2. The method of claim 1, wherein the essential oil is eucalyptus oil.

3. The method of claim 1, wherein the essential oil is in the form of a vapor.

4. The method of claim 3, wherein the concentration of the vapor derived from said essential oil is 500 ppm.

5. A box comprising at least one tomato in combination with an essential oil consisting essentially of 80% cineole for eliciting tomato resistance to *Botrytis cinerea* fungal infection, wherein the tomato is exposed to infection by *Botrytis cinerea*, wherein the essential oil is applied in a sufficient amount to elicit tomato resistance to *Botrytis cinerea* infection, and wherein the essential oil has no direct antifungal effect against *Botrytis cinerea*.

6. The box of claim 5, wherein the essential oil is eucalyptus oil.

7. The box of claim 5, wherein the essential oil is in the form of a vapor.

8. The box of claim 7, wherein the concentration of the vapor derived from said essential oil is 500 ppm.

* * * * *